US008909348B2

(12) United States Patent
Fritsch et al.

(10) Patent No.: US 8,909,348 B2
(45) Date of Patent: Dec. 9, 2014

(54) COCHLEAR IMPLANT STABILIZATION AND POSITIONING DEVICE

(75) Inventors: Michael H. Fritsch, Lincoln, NE (US); John H. Fritsch, Lincoln, NE (US); Josephine Fritsch, Lincoln, NE (US)

(73) Assignee: Domestic Legacy Limited Partnership, Indianapolis, IN (US)

( * ) Notice: Subject to any disclaimer, the term of this patent is extended or adjusted under 35 U.S.C. 154(b) by 577 days.

(21) Appl. No.: 13/065,779

(22) Filed: Mar. 30, 2011

(65) Prior Publication Data

US 2011/0245891 A1 Oct. 6, 2011

Related U.S. Application Data

(60) Provisional application No. 61/341,329, filed on Mar. 30, 2010, provisional application No. 61/341,335, filed on Mar. 30, 2010, provisional application No. 61/341,380, filed on Mar. 30, 2010, provisional application No. 61/341,469, filed on Mar. 31, 2010.

(51) Int. Cl.
*A61N 1/00* (2006.01)
*A61N 1/375* (2006.01)
*A61N 1/05* (2006.01)
*A61N 1/36* (2006.01)

(52) U.S. Cl.
CPC ........... *A61N 1/0541* (2013.01); *A61N 1/36032* (2013.01); *A61N 1/375* (2013.01)
USPC ................. 607/55; 607/57; 607/126; 607/128

(58) Field of Classification Search
USPC ....................................... 607/55, 57, 126, 128
See application file for complete search history.

(56) References Cited

U.S. PATENT DOCUMENTS

| RE31,031 | E | 9/1982 | Kissiah, Jr. |
|---|---|---|---|
| 4,532,930 | A | 8/1985 | Crosby et al. |
| 4,617,913 | A | 10/1986 | Eddington |
| 4,819,647 | A | 4/1989 | Byers et al. |
| 4,832,051 | A | 5/1989 | Jarvik et al. |
| 4,892,108 | A | 1/1990 | Miller et al. |
| 5,123,422 | A | 6/1992 | Charvin |
| 5,571,162 | A * | 11/1996 | Lin ............................... 607/122 |
| 5,653,742 | A | 8/1997 | Parker et al. |
| 5,674,264 | A | 10/1997 | Carter et al. |
| 5,755,747 | A | 5/1998 | Daly et al. |
| 6,112,124 | A | 8/2000 | Loeb |
| 6,151,526 | A | 11/2000 | Tziviskos |

(Continued)

FOREIGN PATENT DOCUMENTS

| EP | 1574181 A1 | 9/2005 |
|---|---|---|
| ES | WO 2004/054474 A1 | 7/2004 |

*Primary Examiner* — Nicole F Lavert
(74) *Attorney, Agent, or Firm* — E. Victor Indiano; Indiano Law Group, LLC

(57) ABSTRACT

A stabilizer is disclosed for use with a cochlear implant receiver stimulator having a body portion and an electrode portion implanted subcutaneously adjacent to a body tissue. The stabilizer is provided for stabilizing the position of the implant receiver relative to the body tissue. The stabilizer has a tissue engaging portion for grippingly engaging the body tissue to fixedly position the stabilizer with respect to the body tissue. The stabilizer also includes a coupler portion for fixedly positioning the stabilizer with respect to the receiver stimulator. The tissue engaging portion and coupler portion cooperatively interact with the receiver stimulator and the body tissue to fix the relative position of the body tissue and receiver stimulator.

17 Claims, 12 Drawing Sheets

(56) References Cited

U.S. PATENT DOCUMENTS

| | | |
|---|---|---|
| 6,205,360 B1 | 3/2001 | Carter et al. |
| 6,301,505 B1 | 10/2001 | Money |
| 6,374,143 B1 | 4/2002 | Berrang et al. |
| 6,408,855 B1 | 6/2002 | Berrang et al. |
| 6,428,484 B1 | 8/2002 | Battner et al. |
| 6,496,734 B1 | 12/2002 | Money |
| 6,537,800 B1 | 3/2003 | Karube et al. |
| 6,549,814 B1 | 4/2003 | Strutz et al. |
| 6,556,870 B2 | 4/2003 | Zierhofer et al. |
| 6,575,894 B2 | 6/2003 | Leysieffer et al. |
| 6,636,768 B1 | 10/2003 | Harrison |
| 6,648,914 B2 | 11/2003 | Berrang et al. |
| 6,724,902 B1 | 4/2004 | Shennib et al. |
| 6,946,851 B2 | 9/2005 | Lee et al. |
| 7,044,942 B2 | 5/2006 | Jolly et al. |
| 7,063,708 B2 | 6/2006 | Gibson et al. |
| 7,146,227 B2 | 12/2006 | Dadd et al. |
| 7,650,194 B2 | 1/2010 | Fritsch et al. |
| 2001/0031974 A1 | 10/2001 | Hadlock et al. |
| 2002/0029074 A1 | 3/2002 | Treaba et al. |
| 2003/0045921 A1 | 3/2003 | Dadd et al. |
| 2003/0097121 A1 | 5/2003 | Jolly et al. |
| 2004/0115241 A1 | 6/2004 | Calhoun et al. |
| 2004/0172118 A1 | 9/2004 | Gibson |
| 2004/0182707 A1 | 9/2004 | Jardemark et al. |
| 2005/0015133 A1 | 1/2005 | Ibrahim et al. |
| 2005/0080473 A1 | 4/2005 | Gibson et al. |
| 2006/0264897 A1 | 11/2006 | Lobl et al. |
| 2007/0060815 A1 | 3/2007 | Martin et al. |
| 2009/0254163 A1* | 10/2009 | Gibson .................. 607/137 |

\* cited by examiner

SURGICAL VIEW OF FACIAL RECESS
WITH ELECTRODE. RIGHT EAR (A) COCHLEAR IMPLANT ELECTRODE (B) FACIAL RECESS WINDOW OF RIGHT EAR
(SURGICALLY CREATED BY DRILLING)

(C) COCHLEOSTOMY OPENING WITH ELECTRODE
ENTERING (D) COCHLEA (E) BONE

COCHLEAR IMPLANT STABILIZATION AND POSITIONING DEVICE

I. PRIORITY STATEMENT

This U.S. non-provisional patent application claims the benefit of and/or priority to Fritsch et al., U.S. provisional patent applications, Ser. No. 61/341,329 filed Mar. 30, 2010 entitled "A Cochlear Implant Electrode Stabilizer Device"; Ser. No. 61/341,335 filed Mar. 30, 2010 entitled "A Cochlear Implant Electrode Bracket Device"; and 61/341,380 filed Mar. 30, 2010 entitled "A Cochlear Implant Pocket Retainer Device"; and Ser. No. 61/341,469 filed 31 Mar. 2010, entitled "Cork for Cochlear Implant." The entire contents of all of the above provisional applications are all specifically incorporated herein by reference.

II. TECHNICAL FIELD OF THE INVENTION

The present invention relates to cochlear implant hearing-aid devices, and more particularly, to a positioning stabilization device that is used to retain and secure a cochlear implant device and electrode at the desired position on the patent within a surgically created tissue pocket.

III. BACKGROUND OF INVENTION

A cochlear implant hearing-aid device is used to help hearing impaired and deaf ears gain awareness and understanding of sound. Normally, the hearing sense is physiologically provided by allowing sound waves to enter the ear canal and vibrate the eardrum and middle ear bones. The bones create a fluid wave inside the cochlea. In the cochlea, cells in the Organ of Corti transform the fluid wave into an electrical nerve impulse that travels to the brain. Once these signals have arrived at the brain, a person realizes "hearing".

The physiological cause of deafness in many individuals is the malfunctioning, or non functioning of the Organ of Corti. Cochlear Implants are needed when there is a hearing-loss due to the absence of sensory portions of the cochlea, but when neural elements are remaining. The cochlear implant hearing-aid device serves as a substitute for the cochlea's Organ of Corti and works by aiding in the creation of hearing by converting sound energy into electrical signals and directly stimulating the neural elements of the cochlea. The implant does this by directly electrically stimulating the remaining nerve fibers that, in a normally functioning ear, would be stimulated by the Organ of Corti.

Typically implants employ a thin wire-like electrode that provides the electrical signal output for stimulating the nerves in the inner ear. The electrode is sized and shaped to fit within the cochlea, and includes a plurality of Astud@-like portions capable of delivering discreet signals to the nerves of the inner ear. The electrode is surgically placed in the cochlea. Examples of cochlear implants are disclosed in the Applicants=earlier applications, including Fritsch et al., U.S. patent application Ser. No. 11/451,715, filed Jun. 13, 2006 (Currently Pending)(Published as US Published Application No. US2007/005117 on 4 Jan. 2007; and the patents and references cited therein, all of which are hereby incorporated by reference. An example of an intra-cochlear implant is shown in the Fritsch et al., U.S. Pat. No. 7,650,194, that issued on 19 Jan. 2010, and an example of an extra-cochlear implant is shown in the Applicants=Fritsch et al., U.S. Published Patent Application, No. US2007/005117 A1, published Jan. 4, 2007.

Most cochlear implants are composed of two main components. The first is an external "Speech Processor" that is worn similarly to a conventional hearing aid. This component receives sound energy and converts that energy into electrical signals. It is mainly devised to convert speech sound energy into electrical energy. The Speech Processor transmits that sound through the skin to an internal component known as the "receiver stimulator". This "receiver stimulator" is commonly referred to as a cochlear implant, and may be an internal implant that includes an electronic housing body portion that is disposed subcutaneously within the tissue near the ear. The receiver-stimulator usually also includes a string or wire like electrode portion that may be implanted internally of the cochlea; (see the '194 patent) or disposed primarily externally of the cochlea (see the Fritsch '117 published application). The body portion of the receiver stimulator receives the electrical signals from a Speech Processor and delivers the electrical impulses into the cochlea via an electrode array.

The receiver-stimulator is implanted surgically within the skull of the patient to be positioned adjacent to, or internally of the patient's cochlea. One surgical trend has been to reduce the impact of surgery on the patient by reducing the size of the incision and tissue exposed during the surgical procedure. Over the last twenty-five years, the incisions and exposure sizes have become smaller and more circumscribed. Presently, a small incision behind the crease of the ear or in the sub-occipital area is used to gain access to the cochlea.

During cochlear implantation surgery, the surgeon must place the stimulating electrode array of the cochlear implant into the cochlea. Initially, the usual microscopic surgical approach creates a "facial recess" window by drilling the bone (FIG. 6) that overlays the cochlea.

Thereafter, the bone overlaying the cochlea is drilled away in order to create an opening into the interior of the cochlea at the turns of the cochlea. This procedure (and the hole formed thereby) is called the cochleostomy.

Once this route of access has been established, the thread-like implant electrode is placed within the interior of the cochlea into the turns of the cochlea. Small grafts of muscle or facia then are packed around the electrode array at the point where the electrode array enters into the interior of the cochlea. The packing seals the cochleostomy site and also slightly stabilizes the electrode array within the cochlea to fix the position of the electrode within the cochlea. Sealing of the cochleosotomy site and securing of the electrode in place are important to prevent migration of the electrode and to prevent fluids from leaking out of the inner ear and for keeping bacteria out. As the position of the electrode within the cochlea significantly impacts the performance of the implant, it is highly desirable to ensure that the implant is properly positioned within the cochlea.

Techniques for sealing the cochleostomy site and securing the electrode include using fascia, Tisseel™ glue, gelfoam, and suture to help maintain the electrode in the desired position. There is a great deal of imprecision in the present technique of sealing the cochleostomy and securing the electrode, as variations occur from surgeon to surgeon and even from surgery to surgery. This imprecision leads to variations in outcome and unwanted electrode movement. An insecure, or imprecise electrode array placement can cause electrode arrays to move away from their intended positions, and cause cochleostomy sites to not seal well.

The consequence of this movement or migration is that sub-ideal or even non-functional electrode positions result. Since the purpose of the electrode is to deliver an electrical charge to a particular set of nerves within the cochlea, it is highly desirable to have the electrode positioned properly adjacent to the nerve group that is intended to be stimulated. Therefore, the movement of the electrode away from its most desirable position adversely impacts the efficiency of the electrical signal transfer between the electrode and the nerve to be stimulated. As such, it would be advantageous to have a better form of stabilization to thereby help to maintain good signal transfer efficiency and thereby provide a better hearing experience for the patient.

The receiver-stimulator includes a proximally disposed body portion that houses the electronics necessary to receive the signals transmitted from the externally disposed speech processor. The proximal body portion is coupled to a relatively distally disposed electrode that has an appearance similar to a "tail" coupled to the body portion "mouse". The electrode portion includes a proximal end and a distal end. The distal end is inserted through the boney wall of the cochlea, and internally within the turns of a cochlea, or is otherwise coupled to the implanted electrode array.

The surgical step to create the final position for receiving the receiver-stimulator implant is known as "creation of a pocket". This pocket is a narrow corridor extending through the tissues ending in a closed distal end like the toe of a sock. The receiver-stimulator is then pushed-up distally into the deepest recess of the pocket, to the blunt ending of the pocket, which is the preferred final position of the receiver stimulator implant. The implant is supposed to heal into position and remain at that point where it is placed deep within the patient. The final position of the receiver stimulator implant, which may vary slightly, is behind and above the ear under the skin.

Unfortunately, the receiver stimulator cannot be secured within the pocket with traditional suture "ties" because it is not reachable when it is placed in the final position in the deepest recess of the pocket. A number of implants that are so placed within pockets will migrate within and out of the pocket. The migration end-point then becomes the permanent position of the receiver-stimulator since the receiver-stimulator heals in place with a scar tissue shell and is immobilized at that point.

The newly migrated receiver-stimulator implant may then be permanently positioned out of position for optimal performance. Most notably, the body portion receiver-stimulator may migrate to a first position low over the ear and interfere with the positioning and retention of the Speech Processor on the ear. The two components (Speech Processor and the body portion of the receiver-stimulator) may also knock against each other causing clicking sounds and disruption of electrical signals. These clicking sounds and electrical signal disruptions can be rather annoying to a patient. The external ear may also be bent in a downward position causing discomfort to the patient.

For the above mentioned reasons, it would be desirable to find a device or method for maintaining the proper positioning of the implanted devices and to limit or eliminate device migration. It is therefore one object of the present invention to provide a device that reduces the likelihood of unwanted movement of the surgically implanted devices after surgery and during the healing process. In particular, it is an object of the present invention to provide a device and method for restricting movement and migration of an intra-cochlear electrode and a receiver stimulator body, to thereby reduce the likelihood of unwanted movement and increase the likelihood that the device will maintain its desired position.

IV. SUMMARY OF THE INVENTION

In accordance with the present invention, a stabilizer is provided for use with a cochlear implant receiver stimulator having a body portion and an electrode portion, that are implanted subcutaneously adjacent to a body tissue. The stabilizer is provided for stabilizing the position of the implant receiver stimulator relative to the body tissue. The stabilizer comprises a tissue engaging portion for grippingly engaging the body tissue to fixedly position the stabilizer with respect to the body tissue. A coupler portion is provided for fixedly positioning the stabilizer with respect to the receiver stimulator. The tissue engaging portion and coupler portion cooperatively interact with the receiver stimulator and body tissue to fix the relative position of the body tissue and receiver stimulator.

The tissue engaging portion can comprise a plurality of barbs. In one embodiment, the plurality of barbs are formed on a casing of the receiver stimulator. In another preferred embodiment, the barbs are formed as part of a cage member having a hollow interior for receiving the receiver stimulator, and an exterior to which is coupled the tissue engaging portion. The tissue engaging portion of the cage embodiment can comprise a plurality of barb members that extend exteriorly outwardly from the cage member.

In another embodiment of the present invention, the tissue engaging portion can comprise a bracket member, and a fastener for coupling the bracket member to the body tissue. The bracket member can include an aperture and the fastener can comprise a longitudinal fastener extendable through the aperture of the bracket member. The coupler portion can include a band member for interiorly receiving the receiver stimulator member. The band member can comprise a ratchet and clip containing pull-tie type clamp member, with the bracket member being generally plate shaped and including a band receiving aperture through which the band member can pass for coupling the band member to the plate-shaped bracket member.

In another embodiment, the stabilizer includes a body member, wherein the body member includes an outer surface and an interior passageway, with the outer surface comprising the tissue engaging portion of the stabilizer, and the interior passageway comprising a coupler portion of the stabilizer. The body member is preferably comprised of a compressible material for permitting the user to compress the body member to reduce the outer surface of the body member prior to the insertion of the body member into a cochlea opening, re-expand the outer surface upon release of the body member after insertion into the opening, and to reduce the diameter of the interior passageway to better secure an electrode portion of a receiver stimulator passing through the interior passageway.

One feature of the present invention is that although it has particular utility when used in connection with hearing aid-type devices, the device is also flexible enough in its potential uses to have utility in connection with other medical applications wherein the need for better stabilization in the area around a surgically implanted electrode is desirable.

These and other features and advantages of the present invention will become apparent to those skilled in the art upon a review of the drawings and detailed description presented below, that represent the best mode of practicing the invention perceived presently by the applicants.

V. BRIEF DESCRIPTION OF DRAWINGS

Figure 8A:
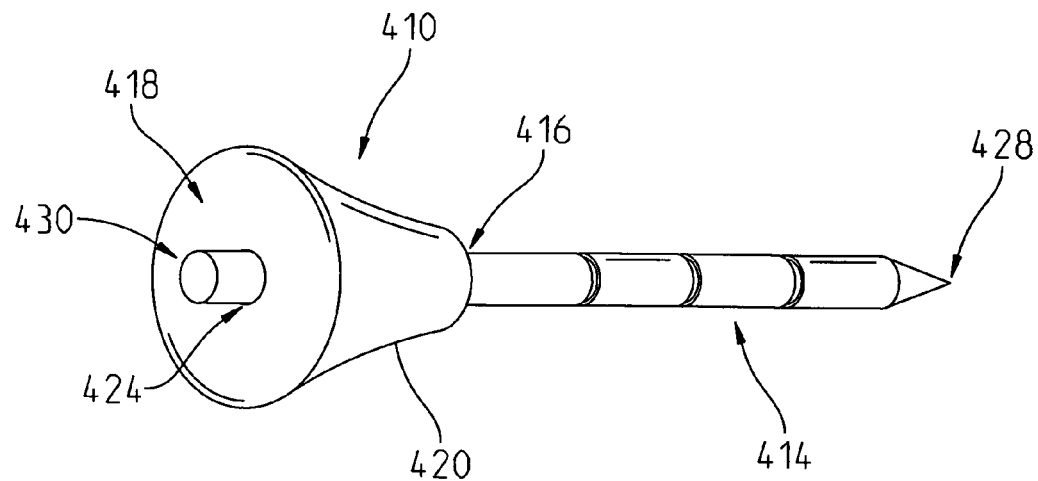
FIG. 8A is a perspective view of a third alternate "cork" embodiment of the present invention, as fitted onto an electrode 414 of a type typically used with a cochlear implant.
Figure 8B:
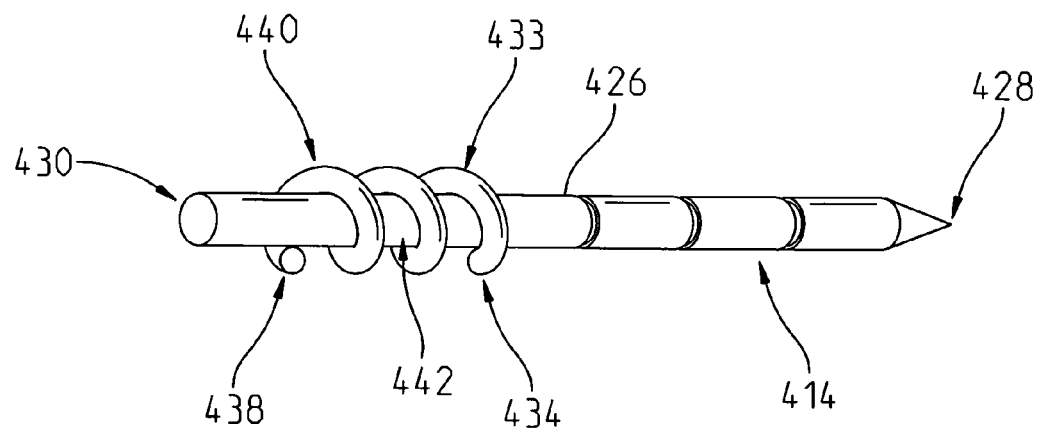
Figure 9:
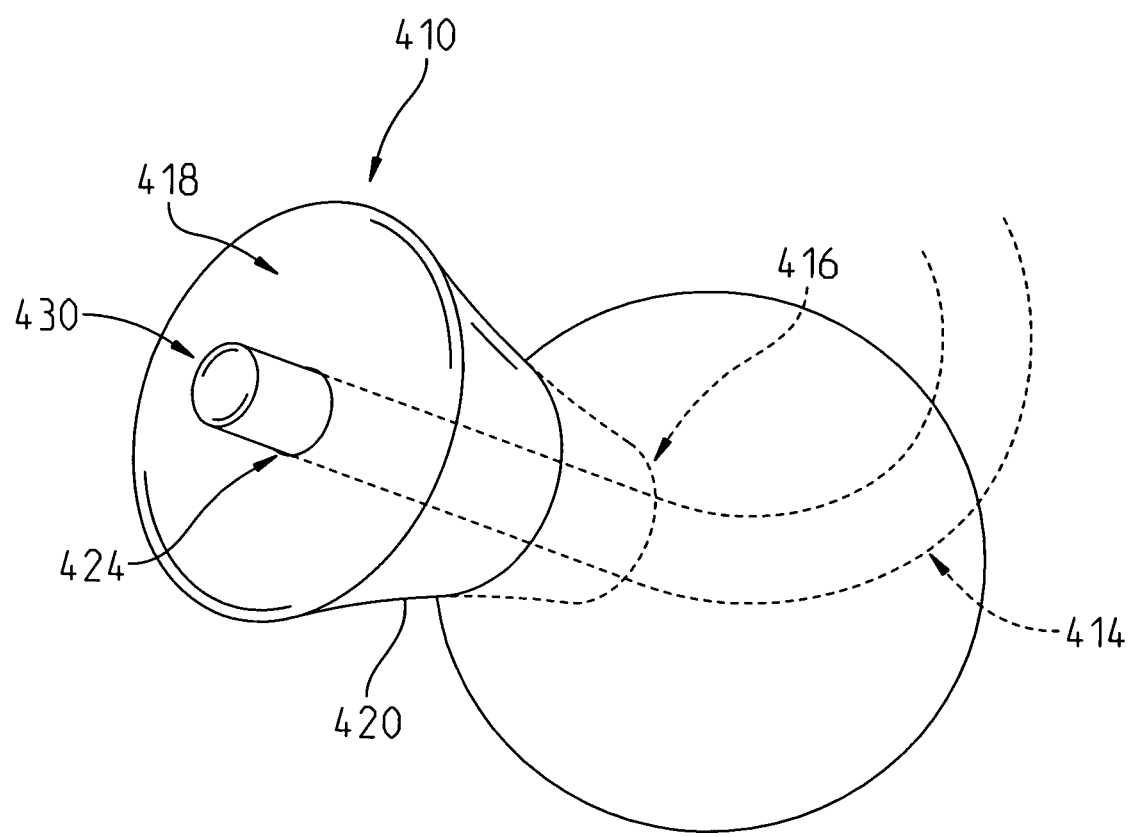
Figure 10A:
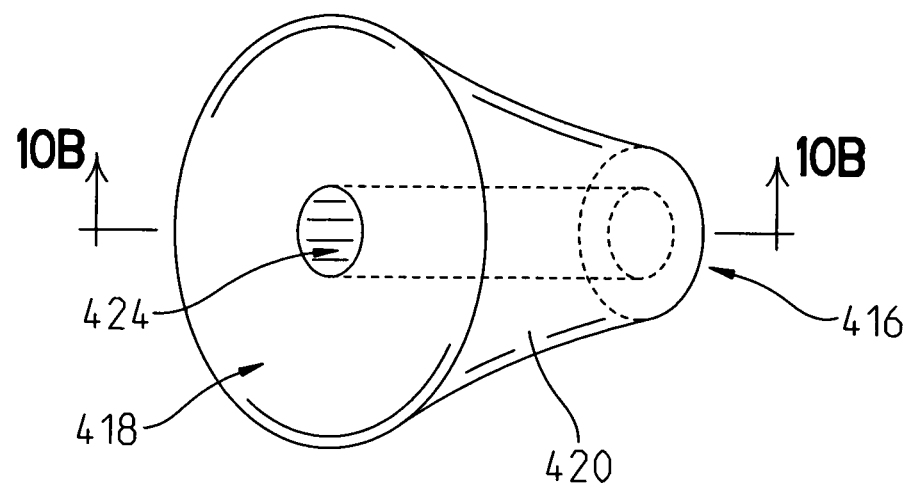
Figure 10B:
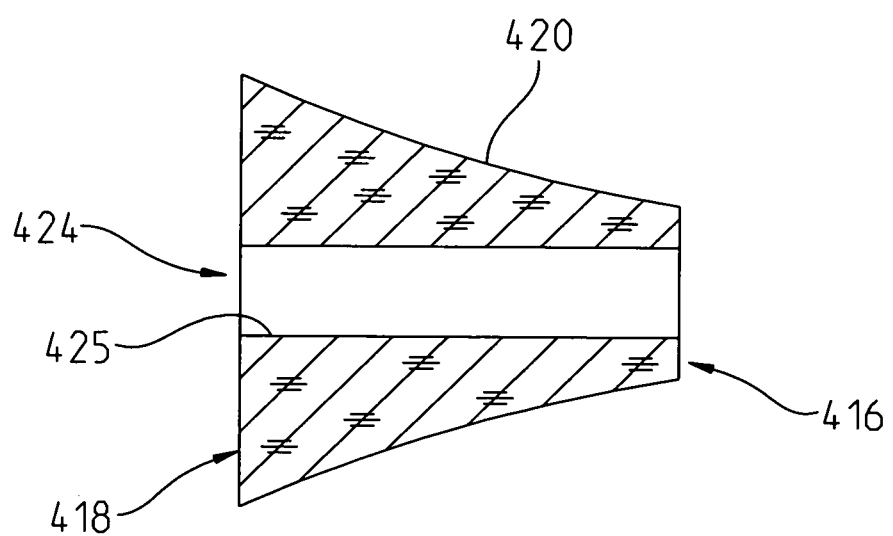
Figure 10C:
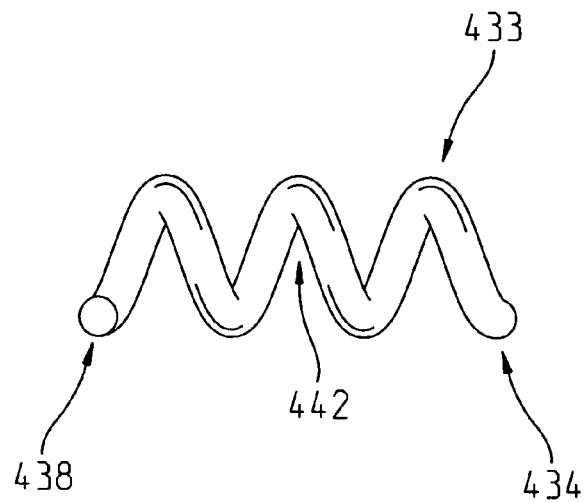
Figure 10D:
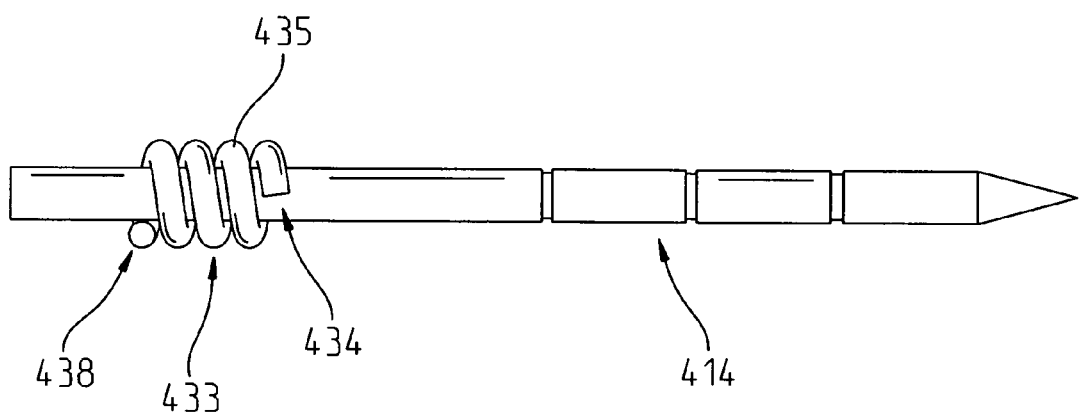

FIG. 8B shows a fourth alternate "helical shaped" embodiment electrode 433 wherein the segments 440 of the helical electrode 433 are wound around the exterior surface 426 of an electrode 414 similar to electrode 414 of FIG. 8 used in connection with a cochlear implant;

FIG. 9 is an enlarged perspective view of the wedge-shaped cork 410 of the third embodiment of the present invention placed in its appropriate position within a cochleostomy opening, so that the outer surface of the wedge-shaped cork 410 is engaged with the bone B of the cochlea;

FIG. 10A is a perspective view showing the central aperture 424 receiver stimulator electrode engaging portion in phantom;

FIG. 10B is a sectional view showing the wedge-shaped side surface 420 of the arcuately wedge shaped cork 410 of the present invention;

FIG. 10C is a side view of a helical cork 433 of the fourth embodiment of the present invention, showing the segments 440 in their expanded position;

FIG. 10D is a side view of the helical-shaped cork 433 of the present invention, showing the helical segments 440 in their compressed configuration, such as when the helical-shaped cork 433 is pressed into a cochleostomy.

VI. DETAILED DESCRIPTION

The present invention relates to a device with multiple features that is intended to better secure an implanted hearing aid device into the tissue of a patient, and seal the wound to facilitate better healing. The implanted hearing aid device, the receiver-stimulator, consists of two main parts; the body member and the electrode array.

In one embodiment, barbs or studs are added to engage body tissue to prevent the migration of the implanted receiver stimulator body within a surgical pocket by fixing the position of the receiver stimulator. In another embodiment, the addition of mounting brackets and clamps to engage the tissue and prevent the migration or movement of the electrode while still in other embodiments compressible stabilizer designed to add stability to the position of the implants and better seal the wound site for improved healing are employed.

Figure 1:
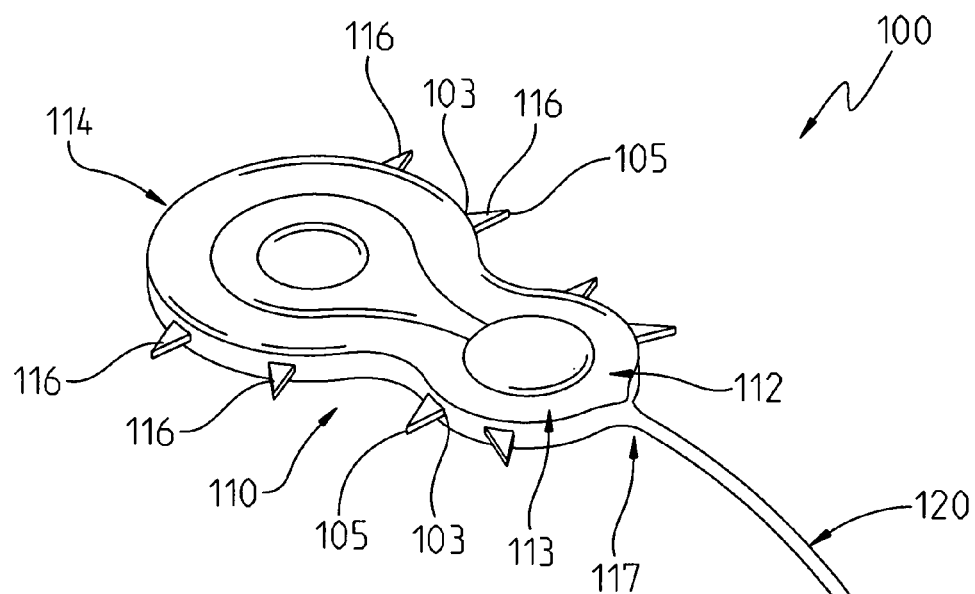
FIG. 1 is a top view of the cochlear implant receiver stimulator
Figure 2:
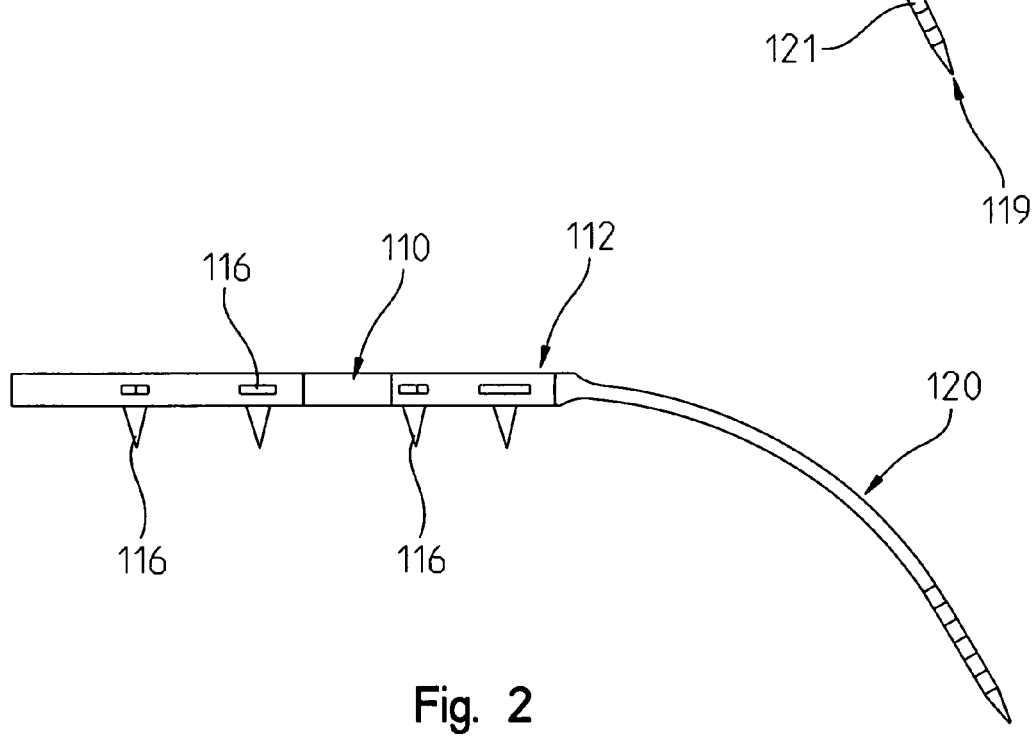
FIG. 2 is a side view of the cochlear implant receiver stimulator
Figure 3:
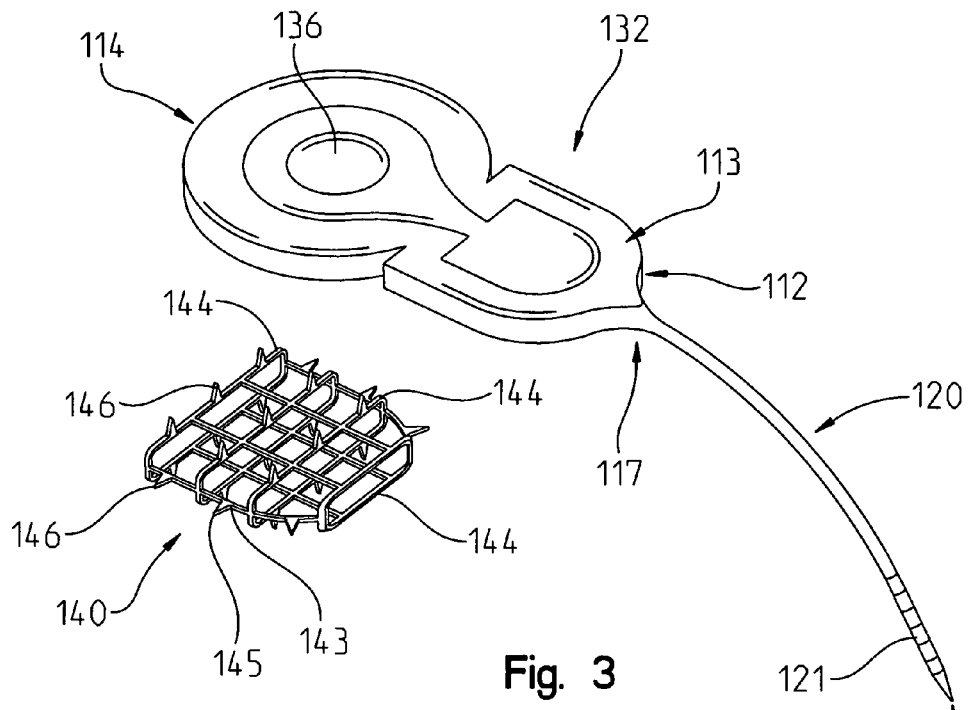
FIG. 3 is a top, exploded view of the cochlear implant receiver stimulator and the cage-like stabilizer retaining device
Figure 4:
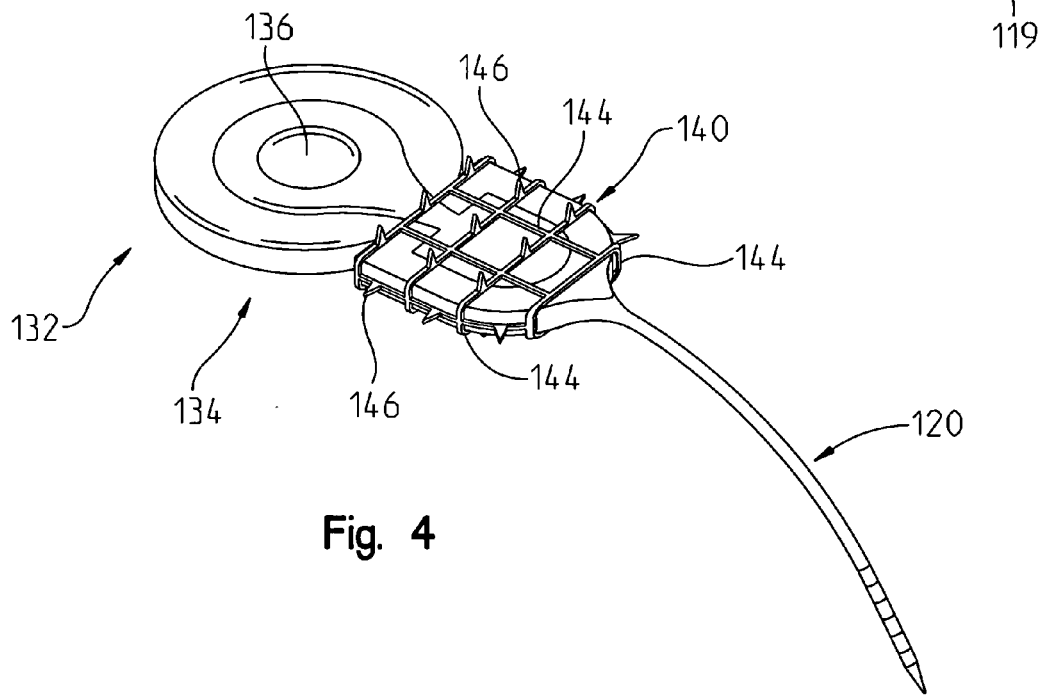
FIG. 4 is a top assembled view of the cochlear implant receiver stimulator device with the cage-like stabilizer device installed.

The first embodiment of the implant device 100 is shown in FIGS. 1 and 2. The cochlear implant receiver stimulator 100 body includes the addition of barbs or studs 116 to the outer portion of the body. These bards or studs 116 engage by piercing into surrounding body tissue to limit or prevent movement of the implant 100. The outwardly protruding barbs or studs 116 may be added by various methods; two of which are described herein. The first is to form the barbs 116 as part of the casing of implant body 100. The barbs 116 become an addition to the actual receiver-stimulator 100 as an extension of metal, plastic, or an absorbable material from the receiver-stimulator 100. The second embodiment is shown in FIGS. 3 and 4 wherein a cage-like wrap-around 140 is provided that envelopes the receiver-stimulator device 121 and includes outwardly protruding stud or bard like projections 146 projecting out from the hollow interior containing cage 140.

The first embodiment implant system 100 is shown in FIGS. 1 and 2 as comprising a cochlear implant receiver-stimulator 100. The receiver stimulator 100 includes a body portion 112. The body portion 112 that includes a casing 113 for internally containing the electronic circuitry necessary for the device 100 to operate. The receiver stimulator 110 also includes a stimulation delivery electrode array 120 that is long and thin and has an appearance similar to a tail. The electrode array includes a proximal end 117 attached to the body portion and a distal end portion 119 that is sized and configured for insertion through a cochleostomy opening into the interior of a cochlea.

A plurality of signal transmitting studs 121 are disposed at the distal end portion 119 for transmitting electrical segments to closely positioned neural receptors for the Organ of Corti. Examples of such stimulation delivery electrode arrays can be found in the Applicants' above referenced patents and applications, and also in some of the patents cited therein. The stimulation delivery electrode arrays 121 deliver the electrical stimulation to the receptors within the cochlea to help stimulate the receptors to send a signal to the brain, and thereby stimulate hearing for the user.

The casing 113 of the stimulator-receiver 110 body portion 112 includes a series of barbs 116 that are formed or joined to the outer surface 114 of the casing 113. The barbs 116 include a proximal end 103 which is coupled to the casing, and a piercing distal end 105 that is provided for grippingly engaging any body tissue it pierces. The barbs 116 are provided for engaging the surrounding body tissue. This engagement between the barbs 116 and the surrounding body tissue helps to fixedly position maintain the cochlear implant body 112 in the proper position.

The second embodiment of the stimulator-receiver 132 body 112 position maintaining device includes a cage-like wrap-around 140 having a hollow interior 141 for receiving the body 112 of implant 121. The cage 140 may be a separate device from the cochlear implant body 112 (FIGS. 3 and 4). The cage 140 may be provided to be separate from body 112, or cage 140 may be coupled to the body 112 of implant receiver-stimulator 132 at the factory and come packaged as an assembled, one piece unit (FIG. 4). The cage 140 may be constructed from any of metal, plastic, composite, or an absorbable material.

Turning now to FIGS. 3 and 4, the assembly 121 includes a cochlear implant receiver-stimulator 132 that includes a body portion 112, including a casing 113 and a side edge 114, and an array of stimulation delivery electrodes 120. A signal providing electrode 120 is provided for delivering a signal to the cochlear implant receiver-stimulator 132 from the signal generating sources such as the speech processor (not shown). A magnet 136 can be provided for helping to position the external speech processor unit.

It will be noted that the body 134 of the cochlear implant 132 has no barbs attached thereto at the side surface 114 of casing 113. Rather, a cage member 140 is provided that has a hollow interior 141 for interiorly receiving the body portion 112 of the receiver stimulator 132. When the receiver stimulator 13 is received within the interior of cage 140, the cage 140 surrounds the exterior of the body 112 of the cochlear implant 138, and is snugly fitted thereto. The cage member 140 includes a plurality of cage framework members 144 having interior surfaces for engaging the cage member 140 to the body 112 of the cochlear implant 132. A series of barbs 146 are formed on, or coupled to the exterior surface of the cage framework members 144 to extend outwardly from the cage 140. The barbs 146 each have a proximal end 143 coupled to the cage and a piercing distal end 145 for grippingly engaging body tissue to thereby position the cage member 140 and the receiver stimulator 132 body in its desired position within the surgically formed pocket in which the receiver stimulator 132 is placed by the surgeon. The barbs 146 serve the same purpose as the barbs 116 shown in FIGS. 1 and 2.

Figure 5A:
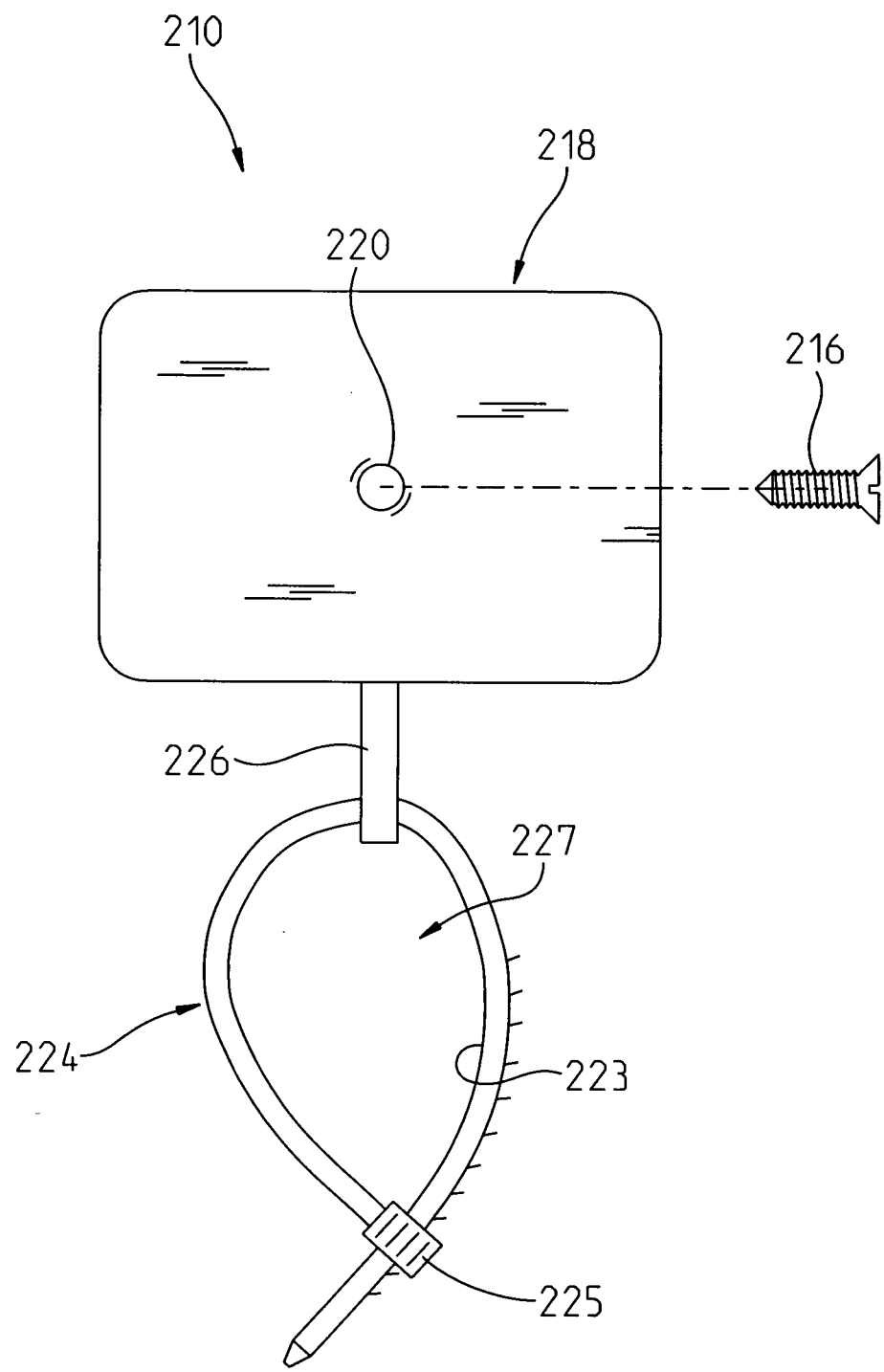
FIG. 5A is a front view of a first alternate embodiment, bracket and clamp assembly type stabilizer of the present invention.
Figure 5B:
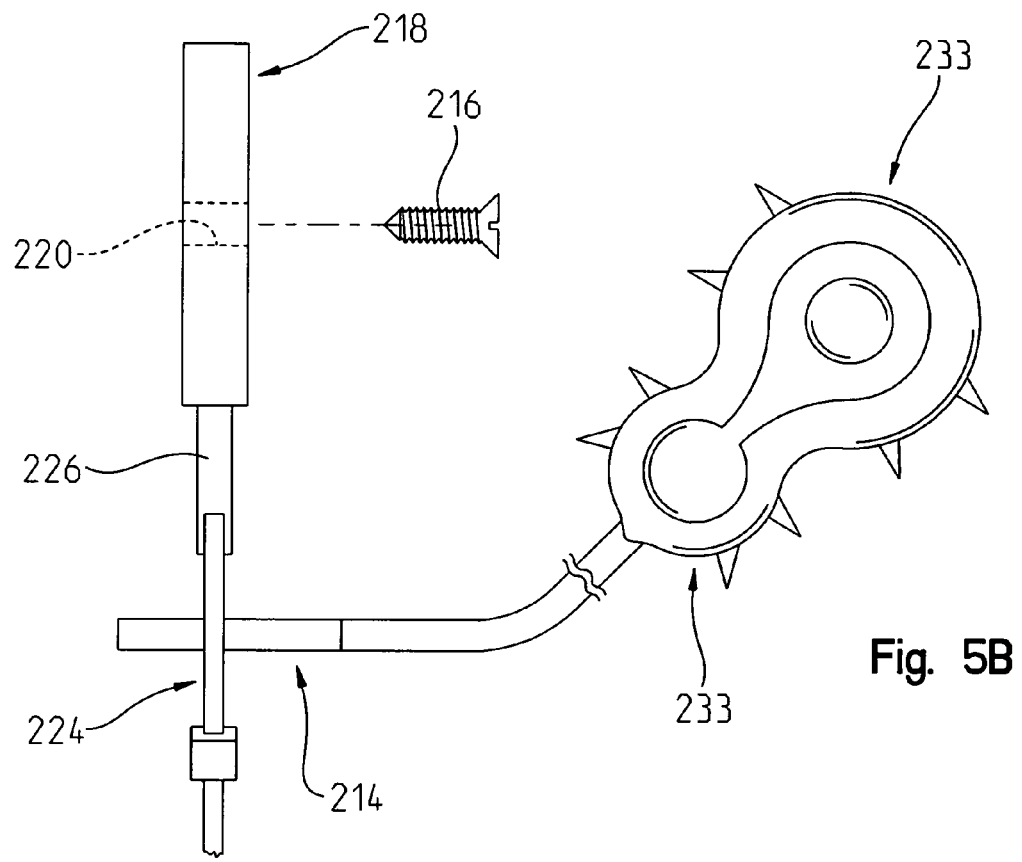
FIG. 5B is a side view of the bracket and clamp assembly of the present invention.
Figure 5C:
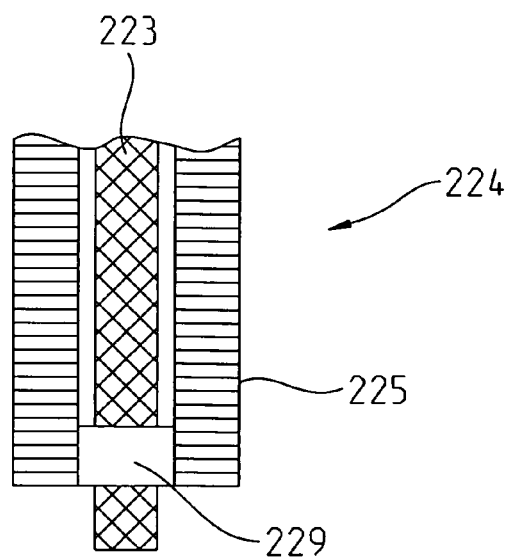
FIG. 5C is a close up, enlarged side, sectional view of the clamp assembly of the embodiment of FIG. 5A.
Figure 5D:
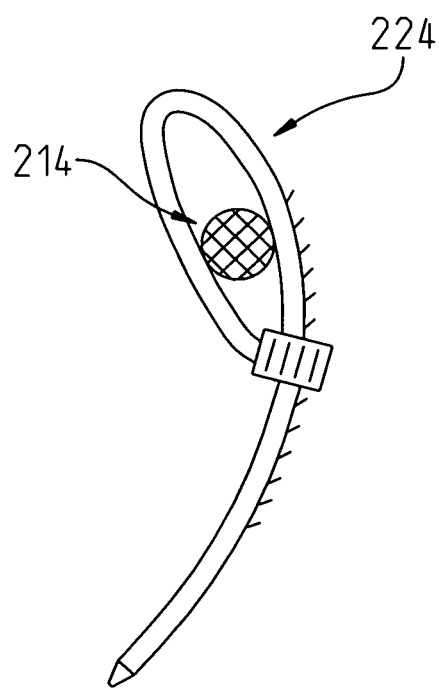
FIG. 5D is an enlarged front view of the clamp member of the embodiment of FIG. 1A of the present invention in a "loose" configuration.
Figure 5E:
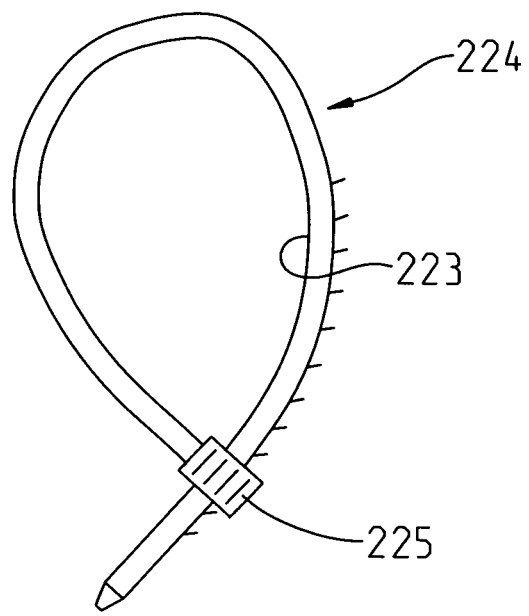
FIG. 5E is an enlarged, front view of the clamp member of FIG. 5D, except wherein the clamp is in a "tightened" configuration.

A bracket assembly 210 can be employed to securely and fixedly position the electrode portion 120 of a receiver-stimulator device (e.g. 233) at its proper place. The bracket mechanism (e.g. 217, FIG. 5A) is used to firmly secure the electrode 120 to the surrounding tissue, and preferably the bone material tissue of the patient in order to prevent migration and movement of the electrode 120.

The cochlear implant electrode bracket device 210 as shown in FIGS. 5A-5E of the present invention is designed to hold the electrode portion 214 of a receiver stimulator 233 firmly in place and prevent migration, and to especially prevent migration of the electrode 214 with the cochlea. The bracket device 210 includes a generally planar plate 218 having an aperture 220 for receiving a fastener, such as a longitudinal type fastener, such as the bone engaging screw 216. Screw 216 can pass through aperture 220 and threadedly engage body tissue and preferably bony body tissue. A clamp receiving loop 226 includes an aperture through which a ratchet containing clamp member such that pull tie 224 can pass. This is done by anchoring the bracket plate 218 with a fastening device 216 that passes through an aperture 220 in the bracket 218, and then into the bone. The bracket 210 plate 218 is then fastened to the electrode 214 by clamping it onto the electrode 214 with a clamp member 220.

The bracket 218 is designed to be mounted on bone surrounding the facial recess (FIG. 1). A 1-2 mm diamond drill, that is used routinely during the surgical implantation procedure, drills a hole into the posterior bony ear canal or a nearby non-vital bony structure. Thereafter, the bracket 210 plate 218 is fixed to the bone using the longitudinal bone screw fastening device 216 that is extended through the fastening device aperture 220. Extending from the bracket 218 is the clamp appendage 226.

The clamp 224 contains a ratchet mechanism that comprises a series of laterally extending ridges formed on an interior surface 223 of the clamp 224, which mate with a ratchet clip 225 disposed at one end of the pull tie 224.

The electrode 214 is then captured and secured in within the interior of the loop of the clamp 224 of the bracket device 218 which is attached via the clamp appendage 226. The bracket 218 is fixedly coupled to the bone through the insertion of the fastening device 216 which passes through the aperture 220. The electrode 214, through its stationary coupling with clamp 224, is thereby fixedly coupled, and stationary positioned in its desired place. The bracket device 218 is solidly mounted to bone, thereby preventing any significant movement of the electrode 214. This helps to assure that the electrode is stationarily positioned for a sufficient time to permit the electrode 214 to become fixed in place by tissue growth and scar tissue growth to thereby provide healing with the electrode 214 in its proper position to help ensure maximum functionality of the electrode 214 after healing.

The bracket device 218 can be made of metal, plastic, nano-materials, or some type of absorbable materials. The device 218 may be coated or impregnated with various chemicals, antibiotics, growth substances, and medications.

The clamp 224 design has functional similarities to a cable tie or "pull-tie". A cable tie usually consists of a sturdy plastic strip having an integrated gear rack 223, and on one end a ratchet 229 within a small open case 225. Once the tip of the cable tie clamp 224 has been pulled through the case 225 and past the ratchet, it is prevented from being pulled backward. The resulting loop 227 may only pull tighter.

Figure 7A:
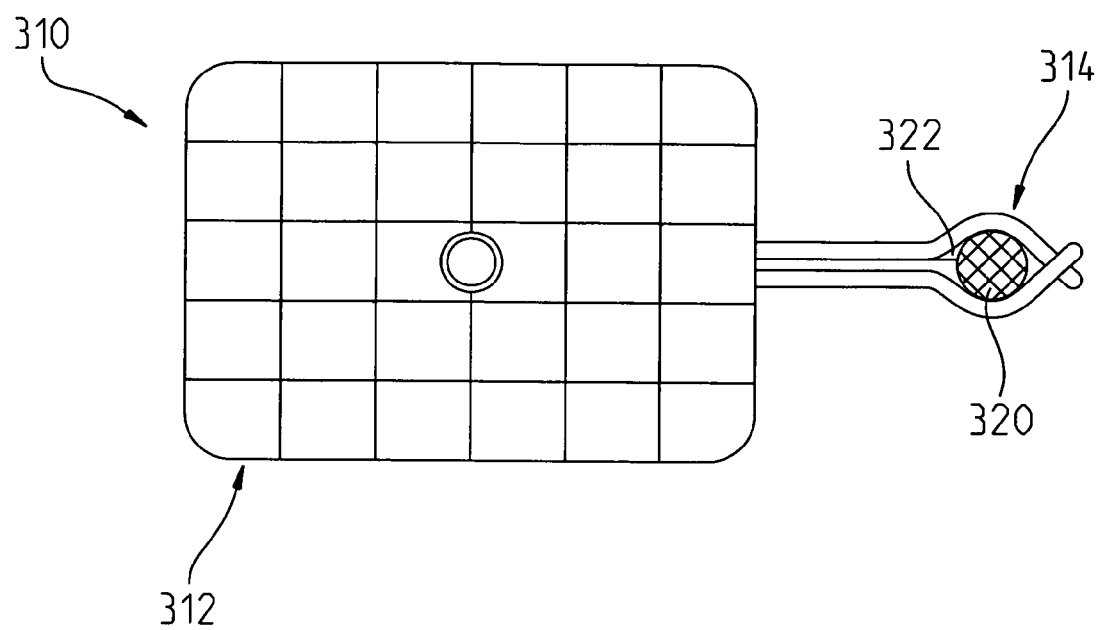
FIG. 7A is a front view of a second alternate embodiment stabilizer of the present invention.
Figure 7B:
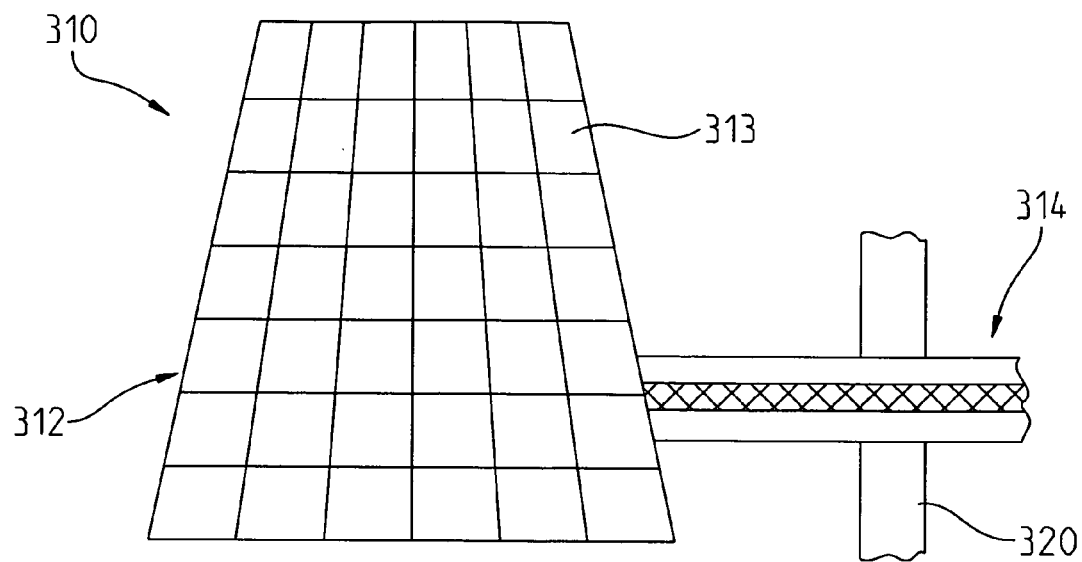
FIG. 7B is a top view of the second alternate embodiment stabilizer of FIG. 7A of the present invention.
Figure 7C:
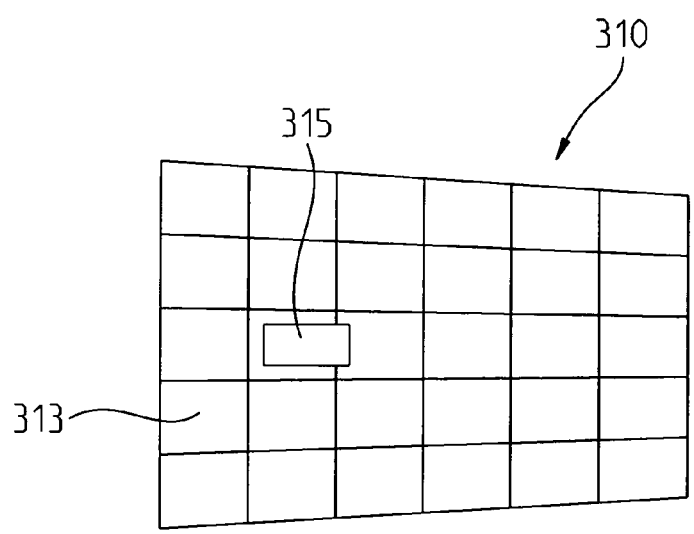
FIG. 7C is a side view of the stabilizer embodiment of FIG. 7A of the present invention.

In addition to the above clamp, it may be desirable to include additional stabilization of the electrode array in order to more securely maintain the desired position. The cochlear implant electrode retainer device 310 shown in FIGS. 7A-7C is designed to hold the electrode 320 firmly in place. It is important to note that this wedge like retainer device 310 can be used with or without the clamp type device as described above. Either device can be used on its own or in conjunction with the other.

The retainer device 310 includes a wedge-like frustoconical body 312 and a clamp-like holder 314. The body 312 holds the retainer device 310 in place with respect to the surrounding patient anatomy. The holder 314 is designed to interiorly receive electrode 320 to thereby clamp onto the electrode 320 to hold the electrode 320 in place with respect to the retainer 310.

The device body 312 is designed to act as a spongy wedge that is "wedged" into placed into the facial recess or neighboring bony place close to the facial recess. Since the body 312 is compressible, the body 312 is preferably compressed before insertion into its final place of insertion. After insertion, the body 312 is allowed to expand into the space permitted by the confines into which it is wedged. When expanded, the outer surface 313 of the body 312, is fixed in place against the surrounding bone.

Figure 6:
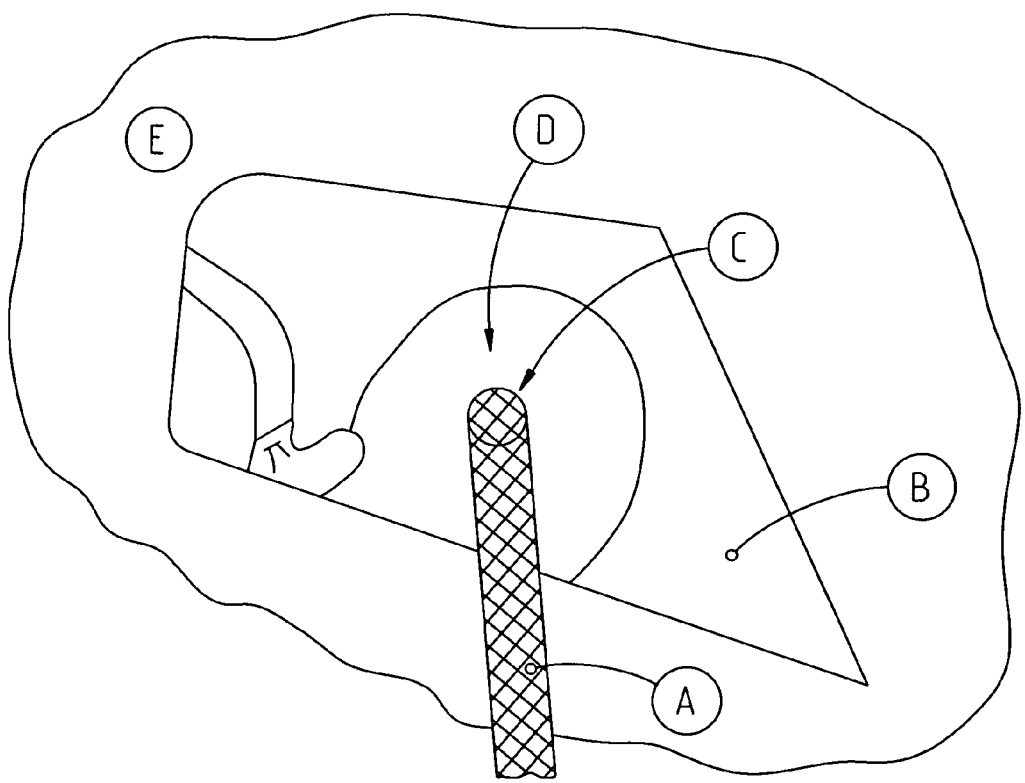
FIG. 6 is a view of a facial recess during surgery, with an electrode implanted adjacent to the right ear of the patient.

The electrode 320 can extend next to the body portion 312 or through an opening 315 through the center of the body portion 312 (FIG. 6). If the electrode 320 passes through the center of the body 312, then the electrode 320 is pinned by the compressive wedge effect exerted on the sides of the opening 315 into a desired position where it is retained.

The holder 314 is designed to act as an attachment clamp to fixedly position the electrode wire 320. The electrode wire 320 is placed into a holding and gripping aperture 322. The holder 314 and a release mechanism engage the clamp 314 tightly around the electrode 320.

Between the actions of the body 312 and the holder 314, the electrode 320 is held firmly in place until the final healing takes place. The clamp 314 is designed to be atraumatic to the electrode 320. The secure stabilization by the stabilizer 310 help to prevent any migration of the implanted electrode 314 away from the final surgical placement. In this way, the likelihood of achieving maximal performance of the electrode 320 enhanced since the electrode 320 is more likely to remain resident in its desired, and most effective position.

The stabilizer device 310 may be made of metal, plastic, composite, or an absorbable material but is preferably made from a hand-compressible material. It may be coated or impregnated with other substances to enhance performance regarding antimicrobial, growth of tissues, and other medication effects.

In addition to stabilization of the electrode, there may be an additional need for better sealing of the cochlea at the surgical site where the electrode passes from inside to outside of the cochlea. The cork like stabilizer device 410 is designed to both seal the cochleostomy and to hold the electrode 414 in place at the cochleostomy site. Wedge-shaped cork 410 of the present invention is shown best in FIGS. 8A, 9, and 10. Wedge shaped cork 410 includes a generally radially extending, planar distal surface 416 ad a radially extending, generally planar proximal surface 418. As used herein, a naming convention will be employed wherein the distal end, such as distal surface 416 of the cork 410 relates to that end that is the "forward end" that is inserted into the cochleostomy, whereas the proximal end 418 is the "nearer" or "rearward" end that will remain exteriorly of the cochleostomy.

Connecting the distal end 416 and the proximal end 418 is a generally frustoconically shaped radially outwardly facing, and axially extending surface 420. An axially extending, central passageway 424 extends axially between the proximal end 418 and the distal end 416 of the cork 410 and is defined by a cylindrically shaped radially inwardly facing wall 425.

As best shown in FIG. 9, when the wedge-shaped cork 410 is inserted into the cochleostomy, the side surface 420 engages the bone B of the Cochlea. When in this position, the wedge-shaped cork 410 is "wedged" into the bone B of the cochlea, to hold the electrode 414 device in place. The electrode 414 that also includes a proximal end 430 and a distal end 428 and a diameter that is sized and shaped to fit snugly within the central aperture 424 of the cork 410.

As will be noted in FIG. 9, the compression of the wedge-shaped cork 410 within the cochleostomy causes a radial compression of the central passageway 424, to help the interior wall 425 grippingly engage the electrode 414, to thereby wedge the electrode 414 within the central passageway 424. Preferably when a wedge shaped cork 410 is inserted into the cochleostomy, so that it engages the bone B, the wedge shaped cork 410 is slightly compressed, to help the tissue engaging radially outwardly facing surface 420 to engage the bone.

An alternate embodiment helically-shaped cork 433 is best shown in FIGS. 8B, 10B and 10C. The helically-shaped cork 433 has a shape generally similar to a coil spring, and includes a distal end 434, and a proximal end 438. The turns 440 of the helically-shaped cork 433 have radially inwardly facing surfaces that define a generally central aperture 442. Central aperture 442 interiorly receives the external surface 426 of the electrode 414. As best shown in FIG. 10B, when the spiral-shaped cork 433 is inserted into the ear, the spirals 440 are compressed, to form a plug, wherein the radially outwardly facing surface 435 of the cork 433 serves as tissue engaging surfaces for grippingly engaging the bone adjacent to the cochleostomy site, to thereby help maintain the spiral cork 433 in engagement with the bone B of the cochlea, and within the cochleostomy.

Turning now to the FIG. 9, the wedge-shaped cork 410 is shaped to fit around the electrode 414 in a donut-like fashion wherein the electrode 414 is interiorly received within aperture 424. The spiral-shaped cork 433 is designed to fit around the electrode 414, in a spiral-like fashion, as shown in FIG. 8B. The cork 410 or 433, may be placed around the electrode 414 by inserting the distal end 428 of the electrode through the central aperture 424, 442 respectively of the corks 410, 433 respectively, and then pulling the corks 410, 433 in a proximal direction, toward the respective proximal end 430 of the electrode 414. Alternately, the cork 410 may include a slit side that enables the wedge-shaped cork 410 to be fitted radially over the exterior surface 426 of the electrode 414.

After the electrode 414 is placed into its final position within the cochlea, the cork 410, 433 is advanced in a distal direction until such point as the distal end 416, 434 of the cork 410, 433 respectively abuts the cochleostomy. Then, due to the shape of the respective corks 410, 433, the corks 410, 433 can be advanced to a position between the electrode and the cochleostomy wall in a circumferential fashion as best shown in FIG. 9. This insertion of the corks 410, 413 into the cochleostomy site can be facilitated by compressing the corks 410, 433 prior to insertion to reduce their size and/or diameter, inserting the corks 410, 433 into the cochleostomy, and then releasing the compressive force on the cork 410, 433 so that the cork can expand against the bone adjacent to the cochleostomy site, to permit the tissue engaging outer surfaces of the corks to grippingly engage the bone to thereby prevent movement.

Wedge-shaped cork 410 in cross section is similar to the shape of two wedges, as best shown in FIG. 10. However, this wedge shape is circumferential in order to seal all cochlea sides. It may be expandable when moist and compressed, to form a better fit. Additionally, the side surface 420 of wedge 410 may be arcuate in cross section.

The cork device 410, 433 can preferably be made of a collagen matrix, polyglucolic acid, polygluconate, or some other absorbable material. The cork device 410, 433 may be coated or impregnated with medications, hydroxyappatite, fibrin products, hydrogel products, bacteriostatic, bacteriocidal, antibiotics or other products to aid in fighting and preventing infection.

Having described the invention and all of its parts with reference to certain preferred embodiments, it will be appreciated that the scope of spirit of the present invention extends will beyond the particular embodiments described herein, and is limited only by the prior art.

What is claimed:
1. A stabilizer for use with a cochlear implant receiver stimulator having a relatively enlarged diameter electrical circuit containing simulator unit having a body portion configured to be implanted subcutaneously exteriorly of a facial recess window, and a relatively smaller diameter electrode portion implanted subcutaneously the electrode portion including an implantable portion that is configured to extend through the facial recess window and is configured and sized to be placeable within a cochlea interior, the stabilizer being provided for stabilizing the position of the implant receiver stimulator relative to the body tissue, the stabilizer comprising a tissue engaging portion comprising a plurality of barbs extending outwardly from the body portion, the barbs being configured for grippingly engaging the body tissue exteriorly of the facial recess window to fixedly position the stabilizer with respect to the body tissue, and a coupler portion configured for fixedly positioning the stabilizer with respect to the receiver stimulator, wherein the tissue engaging portion and coupler portion are configured for cooperatively interact with the receiver stimulator and body tissue to fix the relative position of the body tissue and receiver stimulator, to thereby fix the relative position of the implantable portion of the electrode portion and the cochlea.

2. The stabilizer of claim 1 wherein the body portion of the receiver stimulator includes a casing, and the barbs are coupled to the casing.

3. The stabilizer of claim 2, wherein the barbs are formed as a part of the casing.

4. The stabilizer of claim 1 wherein the stabilizer includes an interior for receiving the body portion of the receiver stimulator.

5. The stabilizer of claim 1 wherein the coupler portion of the stabilizer includes a cage member having an interior for receiving the body portion of the receiver-stimulator and an exterior containing the barbs.

6. The stabilizer of claim 5 wherein the barb members are formed as a part of the cage member.

7. A stabilizer for use with a cochlear implant receiver stimulator having a relatively enlarged diameter electrical circuit containing simulator unit having a body portion configured to be implanted subcutaneously and a relatively smaller diameter electrode portion implanted subcutaneously, the electrode portion including an implantable portion that is configured and sized to be placeable within a cochlea interior, the stabilizer being provided for stabilizing the position of the implant receiver stimulator relative to the body tissue, the stabilizer comprising a tissue engaging portion, configured for grippingly engaging the body tissue to fixedly position the stabilizer with respect to the body tissue, and a coupler portion configured for fixedly positioning the stabilizer with respect to the receiver stimulator, wherein the tissue engaging portion comprises a bracket member and a fastener for coupling the bracket member to a body tissue, the tissue engaging portion and coupler portion being configured to cooperatively interact with the receiver stimulator and body tissue to fix the relative position of the body tissue and receiver stimulator, to thereby fix the relative position of the implantable portion of the electrode portion and the cochlea.

8. The stabilizer of claim 7 wherein the bracket member includes an aperture and the fastener comprises a longitudinal fastener extendable through the aperture of the bracket member, the longitudinal portion including a pointed tail configured for being driven into a body tissue for securing and fixedly positioning the bracket member to the body tissue.

9. The stabilizer of claim 7 wherein the coupler portion includes a band member for interiorly receiving the receiver stimulator member.

10. The stabilizer of claim 9 wherein the band members include a ratchet member for permitting the size of the interior of the band member to be fixed at a variation of plurality of different sizes.

11. The stabilizer of claim 10 wherein the band member comprises a ratchet and clip containing pull tie member, and the bracket member is generally plate-shaped and includes a band receiving aperture through which the band member can pass for coupling the band member to the plate-shaped bracket member.

12. The stabilizer of claim 11 wherein the longitudinal fastener comprises a screw and the body tissue comprises a bone type body tissue.

13. The stabilizer of claim 9 wherein the band is sized and positioned for receiving and stabilizing the electrode portion of the receiver stimulator.

14. A stabilizer for use with a cochlear implant receiver stimulator having a relatively enlarged diameter electrical circuit containing simulator unit having a body portion configured to be implanted subcutaneously and a relatively smaller diameter electrode portion implanted subcutaneously, the electrode portion including an implantable portion that is configured and sized to be placeable within a cochlea interior, the stabilizer being provided for stabilizing the position of the implant receiver stimulator relative to the body tissue, the stabilizer comprising a tissue engaging portion, configured for grippingly engaging the body tissue to fixedly position the stabilizer with respect to the body tissue, and a coupler portion configured for fixedly positioning the stabilizer with respect to the receiver stimulator wherein the stabilizer includes a body member, and wherein the body member includes an outer surface and an interior passageway, wherein the outer surface comprises the tissue engaging portion and the interior passageway comprises the coupler portion, and wherein the body member includes a relatively smaller diameter distal end portion and a relatively larger diameter proximal end portion, wherein the distal end portion is sized for insertion into an opening formed in a cochlea, for permitting exterior surface of the body member to grippingly engage bony structure adjacent to the opening formed in the cochlea and wherein the body member is comprised of a compressible material for permitting the user to compress the body member to reduce the outer surface of the body member prior to the insertion of body member into the cochlea opening, re-expand the outer surface upon release of the body member after insertion into the opening, and to reduce the diameter of the interior passageway to better secure the electrode portion passing through the interior passageway.

15. A stabilizer for use with a cochlear implant receiver stimulator having a relatively enlarged diameter electrical circuit containing simulator unit having a body portion configured to be implanted subcutaneously and a relatively smaller diameter electrode portion implanted subcutaneously, the electrode portion including an implantable portion that is configured and sized to be placeable within a cochlea interior, the stabilizer being provided for stabilizing the position of the implant receiver stimulator relative to the body tissue, the stabilizer comprising a tissue engaging portion, configured for grippingly engaging the body tissue to fixedly position the stabilizer with respect to the body tissue, and a coupler portion configured for fixedly positioning the stabilizer with respect to the receiver stimulator, wherein the stabilizer includes a body member that includes the tissue engaging portion and coupler portion wherein the body member is comprised of a compressible material for permitting the user to compress the size of the body member to permit the body member to be inserted into an opening in the cochlea, and then released to engage body tissue adjacent to the opening.

16. The stabilizer of claim 15 wherein the body member is helically shaped and includes a radially inwardly facing surface that defines an axially extending passageway through which the receiver stimulator can pass and wherein the radially inwardly facing surface comprises the coupler portion, the body member also including a radially outwardly facing surface comprising the tissue engaging portion configured for grippingly engaging the body tissue.

17. The stabilizer of claim 16 wherein the axially extending passageway receives the electrode portion of the receiver stimulator.

* * * * *